US008546342B2

(12) United States Patent
Lines

(10) Patent No.: US 8,546,342 B2
(45) Date of Patent: Oct. 1, 2013

(54) COMPOSITION FOR TREATING MENTAL HEALTH DISORDERS

(76) Inventor: Thomas Christian Lines, Hassel (LU)

( * ) Notice: Subject to any disclaimer, the term of this patent is extended or adjusted under 35 U.S.C. 154(b) by 0 days.

(21) Appl. No.: 13/409,902

(22) Filed: Mar. 1, 2012

(65) Prior Publication Data

US 2012/0225833 A1 Sep. 6, 2012

Related U.S. Application Data

(63) Continuation of application No. 11/364,136, filed on Feb. 27, 2006, now abandoned.

(60) Provisional application No. 60/657,344, filed on Feb. 28, 2005.

(51) Int. Cl.
| A61K 31/7048 | (2006.01) |
| A61K 31/352 | (2006.01) |
| A61P 25/22 | (2006.01) |
| A61P 25/24 | (2006.01) |

(52) U.S. Cl.
USPC .......................................... 514/27; 514/454

(58) Field of Classification Search
USPC .................................................. 514/27, 454
See application file for complete search history.

(56) References Cited

U.S. PATENT DOCUMENTS

| 4,705,796 | A | 11/1987 | Hendry et al. |
| 6,551,629 | B1 | 4/2003 | Gorsek |
| 6,572,272 | B2 | 6/2003 | Blechman |
| 6,576,272 | B1 | 6/2003 | Blechman |
| 6,579,543 | B1 | 6/2003 | McClung |

FOREIGN PATENT DOCUMENTS

| CN | 1398868 | 2/2003 |
| CN | 1408396 | 4/2003 |
| CN | 1663477 | 9/2005 |
| DE | 10004547 | 8/2001 |
| DE | 101 45 129 | 3/2003 |
| JP | 2000-256206 | 9/2000 |
| WO | WO 97/46234 | 12/1997 |
| WO | WO 02/062367 | 8/2002 |

OTHER PUBLICATIONS

Disanto (Resveratrol and quercetin down-regulated tissue factor expression by human stimulated vascular cells, Journal of Thrombosis and Haemostatasis, 2003,1, pp. 1089-1095).
Trout (Vitamin C and cardiovascular risk factors, , Am J. Clin Nutr, 1991, 53: pp. 322S-325S).
Ganji (Niacin and cholesterol: role in cardiovascular disease (Review), Journal of Nutritional Biochemistry, 2003, 14, pp. 298-305).
Chen (Quercetin, a phytoestrogen and dietary flavoinoid, activates different membrane-bound guanylate cyclase osoforms in LLC-PK1 and PC 12 cell, Journal of Pharmacy and Pharmacology, 2003, 55; 353-358).
Belinky (The antioxidative effects of the isoflavan glabridin on endogenous constituents of LDL during its oxidation, Atherosclerosis 137 (1998) , p. 49-61).
Ajay et al., "Effects of Flavonoids on Vascular Smooth Muscle of the Isolated Rat Thoracic Aorta", Life Sciences 74:603-612, 2003.
Anjaneyulu et al., "Quercetin, a Bioflavonoid, Attenuates Thermal Hyperalgesia in a Mouse Model of Diabetic Neuropathic Pain", Progress in Neuro-Psychopharmacology & Biological Psychiatry 27:1001-1005, 2003.
Banks et al., "A New Natural Stilbene Glucoside From *Rheum rhaponticum* (Polygonaceae)", Aust. J. Chem. 24:2427-2430, 1971.
Dhingra et al., "Memory Enhancing Activity of *Glycyrrhiza glabra* in Mice", Journal of Ethnopharrnacology 91:361-365, 2004.
Granados-Soto et al., "The Peripheral Antinociceptive Effect of Resveratrol is Associated with Activation of Potassium Channels", Neuropharmacology 43:917-923, 2002.
Hatano et al., "Phenolic Constituents of Licorice, IV. Correlation of Phenolic Constituents and Licorice Specimens from Various Sources, and Inhibitory Effects of Licorice Extracts on Xanthine Oxidase and Monoamine Oxidase", Yakugaku Zasshi, 111(6) 311-321, 1991.
Kusano et al., "Inhibition of Adenosine 3',5'-Cyclic Monophosphate Phosphodiesterase by Flavonoids from Licorice Roots and 4-Arylcoumarins", Chern. Pharrn. Bull. 39:930-933, 1991.
Lines et al., FRS 1000, an Extract of Red Onion Peel, Strongly Inhibits Phosphodiesterase 5A (PDE 5A), Phytomedicine, 13(4) 236-239, 2006.
Mitscher et al., "Antimicrobial Agents from Higher Plants. Antimicrobial Isoflavanoids and Related Substances from *Glycyrrhiza glabra* L. var. *typica*", Journal of Natural Products 43:259-269, 1980.
Orsini et al., "Isolation, Synthesis, and Antiplatelet Aggregation Activity of Resveratrol 3-o-β-D-Glucopyranoside and Related Compounds", J. Nat. Prod. 60:1082-1087, 1997.
Rahman et al., "Flower Pigments. Flavonoids from *Argemone mexicana* Linn. (Papaveraceae)", Journal of Organic Chemistry, 29(1),153-155,1962.
Saitoh et al., "New Isoflavan and Flavanone from Licorice Root", Chern. Pharrn. Bull. 24:752-755, 1976.
Westerhoff et al., "Biorelevant Dissolution Testing of St. John's Wort Products", Journal of Pharmacy and Pharmacology 54: 1615-1621, 2002.
Youdim et al., Flavonoid Permeability Across an In Situ Model of the Blood-Brain Barrier, Free Radical Biology & Medicine 36:592-604, 2004.

*Primary Examiner* — San-Ming Hui
*Assistant Examiner* — Kathrien Cruz
(74) *Attorney, Agent, or Firm* — Cesari and McKenna, LLP

(57) ABSTRACT

A composition of three compounds each selected from a selective re-uptake inhibitor of serotonin, a monoamine oxidase inhibitor, and a phosphodiesterase inhibitor, such that all three compounds are different and are naturally occurring.

24 Claims, No Drawings

COMPOSITION FOR TREATING MENTAL HEALTH DISORDERS

CROSS-REFERENCE TO RELATED APPLICATIONS

This application is a continuation of U.S. application Ser. No. 11/364,136 filed on Feb. 27, 2006, which claims the benefit of U.S. Provisional Application No. 60/657,344 filed on Feb. 28, 2005. The contents of the above-referenced applications are incorporated herein by reference in their entirety.

BACKGROUND

Depression and anxiety are caused by numerous factors, including conscious fears, subconscious fears, and stress. They are debilitating conditions that can severely affect an individual. For example, chronic anxiety impairs serotonin synapse uptake and depletes adrenal glands. As another example, stress lowers opioid levels in an individual, causing a sense of urgency, irritability, and depression. Regulating neurotransmitters in the brain is viewed as an important way to treat depression and anxiety.

Combinations of drugs are commonly used to treat life-threatening diseases such as HIV and various cancers. However, this approach has not been commonly adopted to treat less serious disorders in part because of possible side effects.

SUMMARY

The present invention relates to a composition containing three naturally occurring compounds. The composition is effective in treating depression or anxiety.

In one aspect, this invention features a composition that includes three different, naturally-occurring compounds, which are a serotonin re-uptake inhibitor, a monoamine oxidase inhibitor, and a phosphodiesterase inhibitor, respectively. Each of the three compounds can be provided as a plant extract or in pure form (obtained by chemical synthesis or isolated from a natural source). For example, in a composition containing glabridin, resveratrol, and quercetin, glabridin can be provided as a plant extract; and resveratrol and quercetin can be provided in pure form. The composition can further includes vitamin C or vitamin B3.

The composition of this invention can be in dry form or in aqueous form. It can be a drink, a food product, a dietary supplement, or a pharmaceutical formulation. Examples include tea (e.g., a tea drink and the contents of a tea bag), juice (e.g., a fruit extract and a juice drink), soft drink, milk, coffee, cookie, cereal, chocolate, snack bar, jelly, ice cream, yogurt, candy, tablet, tonic, lozenge, or spray.

Lactose and corn starch are commonly used as diluents for capsules and as carriers for tablets. Lubricating agents, such as magnesium stearate, are typically added to form tablets.

The composition of this invention can include a sweetener such as sorbitol, maltitol, hydrogenated glucose syrup, hydrogenated starch hydrolysate, high fructose corn syrup, cane sugar, beet sugar, pectin, or sucralose.

In another aspect, this invention features a method of treating depression, such as a major depressive disorder, an atypical depression, a bipolar disorder, or a dysthymic disorder. In a further aspect, this invention features a method of treating anxiety, such as a panic disorder, a phobia, an obsessive-compulsive disorder, a posttraumatic stress disorder, or a generalized anxiety disorder.

The details of one or more embodiments of the invention are set forth in the description below. Other features, objects, and advantages of the invention will be apparent from the description and from the claims.

DETAILED DESCRIPTION

A composition of this invention contains a naturally occurring compound that inhibits serotonin re-uptake (e.g., glabridin or isoquercetin), a naturally occurring compound that inhibits monoamine oxidase (e.g., glabridin, resveratrol, or quercetin), and a naturally occurring compound that inhibits phosphodiesterase (e.g., glabridin or quercetin). The composition influences one or more of the neurotransmitters in the brain by inhibiting selective re-uptake of serotonin, monoamine oxidase, and phosphodiesterase (e.g., PDE4 and PDE5).

Serotonin (i.e., 5-hydroxytryptamine), a monoamine neurotransmitter, plays an important role in depression, bipolar disorder, and anxiety. Serotonin levels are influenced by inhibition of monoamine oxidase and of selective serotonin reuptake. Monoamine oxidase inhibitors prevent the breakdown of monoamine neurotransmitters (including serotonin) and therefore increase concentrations of the neurotransmitter in the brain. Selective serotonin re-uptake inhibitors block the re-uptake of serotonin, making it stay in the synapse longer. Phosphodiesterase is an enzyme that catalyzes the hydrolysis of phosphodiester bonds, for example, that in cyclic adenosine monophosphate (cAMP) or cyclic guanosine monophosphate (cGMP). cAMP is important for intracellular signal transduction, for activation of protein kinases, and to regulate the passage of $Ca^{2+}$ through ion channels. Decomposition of cAMP to adenosine monophosphate is catalyzed by phosphodiesterase. Inhibitors of phosphodiesterase prevent the hydrolysis of the phosphodiester bond.

Glabridin, present in licorice extract, possesses antimicrobial, anti-inflammatory and cardiovascular protective activities. Resveratrol, present largely in the skins of red grapes, is a polyphenolic antioxidant, an anti-cancer agent, and a phytoestrogen. Quercetin, present mainly in apples, onions, and black tea, is an antioxidant, an anti-cancer agent, and a phytoestrogen. Isoquercetin, present in St John's wort, ginkgo biloba and mountain ash fruit, is also an antioxidant, an anti-cancer agent, and a phytoestrogen.

Depression is a mental disorder characterized by feelings of sadness, loneliness, despair, low self-esteem, and self-reproach. Accompanying signs include psychomotor retardation or less frequently agitation, withdrawal from social contact, and vegetative states such as loss of appetite and insomnia. Examples include a major depressive disorder, an atypical depression, a bipolar disorder, and a dysthymic disorder. Major depressive disorder is also known as major depression, clinical depression, or unipolar depression. To be diagnosed with major depressive disorder, a subject must suffer from at least one of the following three abnormal moods: (1) abnormal depressed mood most of the day, nearly every day, for at least 2 weeks, (2) abnormal loss of all interest and pleasure most of the day, nearly every day, for at least 2 weeks, and (3) if 18 or younger, abnormal irritable mood most of the day, nearly every day, for at least 2 weeks. Atypical depression is a type of depression in which the depressed subject experiences mood reactivity. In addition, a subject suffering from atypical depression has at least two of the following symptoms: increase in appetite or weight gain, excessive sleeping, leaden paralysis, and sensitivity to rejection. Bipolar disorder, also known as manic-depressive illness, is a type of disorder that causes unusual shifts in a subject's mood, energy, and ability to function. Bipolar disorder causes dramatic mood swings from overly high or manic moods to sad and hopeless or depressive moods, with periods of normal moods in between. Severe changes in energy and behavior accompany these changes in mood. Dysthymic disorder is a type of depression in which the subject suffers from a depressed mood for most of the day, for more days than not, and for at least 2 years (in children and adolescents, the duration must be at least 1 year). Further symptoms of dysthymic disorder are two or more of the following symptoms: poor appetite or overeating, insomnia or hypersomnia, low energy or fatigue, low self-esteem, poor concentration or difficulty making decisions, and feelings of hopelessness. During the 2-year period of the disturbance, the subject is not free of the above symptoms for more than 2 months at a time.

Anxiety is a complex combination of a feeling of fear, apprehension and worry often accompanied by physical sensations such as palpitations, chest pain, and shortness of breath. A chronically recurring case of anxiety that has a serious effect on a subject's life may be clinically diagnosed as an anxiety disorder. Examples include panic disorder, phobias, obsessive-compulsive disorder, posttraumatic stress disorder, and generalized anxiety disorder. Panic disorder is a disorder in which the person suffers brief attacks of intense terror and apprehension that cause trembling, shaking, dizziness, and difficulty breathing. A subject who suffers from sudden bouts of intense anxiety is considered to be afflicted with panic disorder. Phobias are a type of anxiety disorder that involve a strong, irrational fear and avoidance of an object or situation. The person knows the fear is irrational, yet the anxiety remains. Phobic disorders differ from other anxiety disorders because there is a specific stimulus or situation that elicits a strong fear response. Obsessive-compulsive disorder is a type of anxiety disorder that is manifested in a variety of forms, but is most commonly characterized by a subject's obsessive drive to perform a particular task or set of tasks, compulsions commonly termed rituals. Posttraumatic stress disorder is a type of anxiety disorder caused by exposure to a stressful or traumatic experience, which may involve near death or serious physical injury. Symptoms can include re-experiencing phenomena such as nightmares and flashbacks, emotional detachment, hyperarousal with sleep abnormalities, extreme distress, and irritability. Generalized anxiety disorder is a type of anxiety disorder that is characterized by uncontrollable worry about everyday, mundane events. The frequency, intensity, and duration of the worry are disproportionate to the actual source of worry, and interferes with daily functioning.

The compounds in the composition of this invention can be acquired by any suitable means, e.g., purchased from commercial sources, prepared from various plants, or prepared by chemical synthesis. Each of the extracts mentioned above can be prepared by first immersing a pulverized plant (or a part of a plant) in an aqueous solvent, an organic solvent, or a mixture of solvents. Examples of a suitable organic solvent include ethanol, dichloromethane, or hexane. The crude extract thus obtained can be filtered or centrifuged to remove any insoluble materials. A purified extract can then be obtained from the crude extract using liquid chromatography (e.g., high-pressure liquid chromatography) or other suitable methods. An extract can be produced either by a batch method or by a continuous method.

A method for preparing resveratrol by chemical synthesis is provided herein.

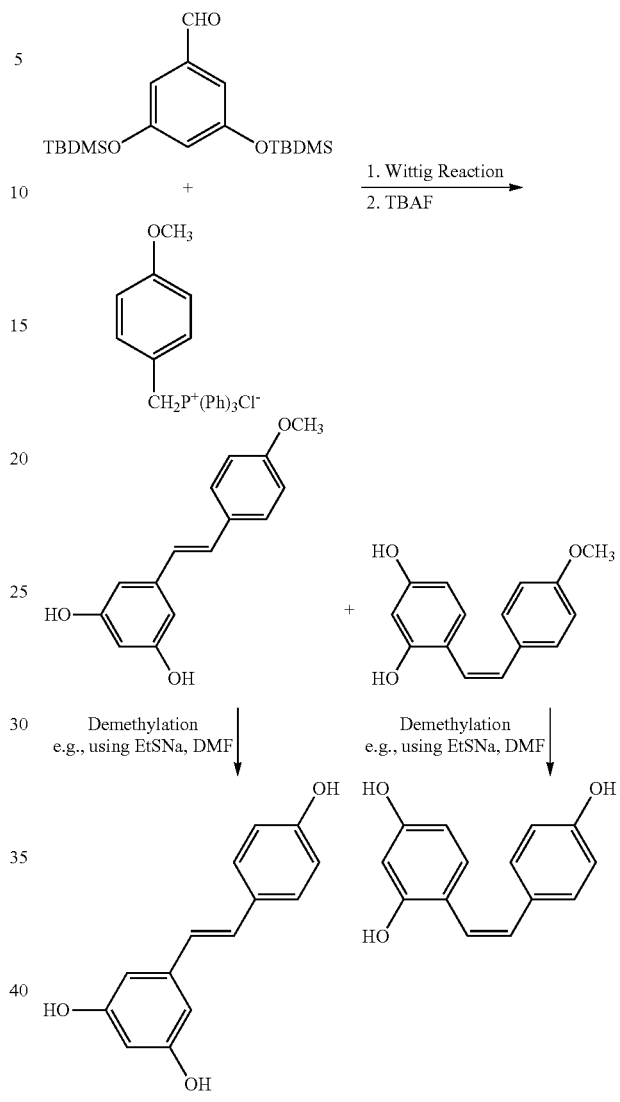

Scheme 1. Synthesis of E and Z forms of resveratrol.

As shown in scheme 1 above, a Wittig reaction between the phosphonium salt of 4-methoxybenzyl chloride and 3,5-bis [tert-butyldimethylsilyl)oxy]benzaldehyde followed by desiliylation with tetrabutylammonium fluoride yields a mixture of E and Z forms of methoxy protected resveratrol. The E and Z forms of methoxy protected resveratrol can be separated using flash column chromatography. The methoxy groups can be deprotected using a suitable reagent, e.g., sodium ethanethiolate in dimethyl formamide, to yield the E and Z forms of resveratrol.

The compounds in the composition of this invention can be provided as a plant extract or in pure form. For example, glabridin can be provided as an extract of licorice (especially licorice root), quercetin can be provided as an extract of onion, grape seed, or berries, and resveratrol can be provided as an extract of red grape skin, isoquercetin can be provided as an extract of ginkgo biloba, St John's wort, mountain ash fruit, or Apocynum venetum L. The term "pure form" covers compounds provided in greater than or equal to 80% purity, greater than or equal to 85% purity, greater than or equal to 90% purity, greater than or equal to 95% purity, greater than or equal to 98% purity, or greater than or equal to 99% purity. It also covers compounds that are diasteromerically or enantiomerically pure.

An effective amount of the composition of this invention, in any of the forms described above, can be administered to a subject for treating depression or anxiety. The term "effective amount" refers to a dose of the composition that is sufficient to provide a therapeutic benefit on a subject. Both in vivo and in vitro studies can be conducted to determine optimal administration routes and doses. The term "administration" covers both oral and parenteral delivery to a subject a composition of this invention in a suitable form, e.g., food product, beverage, tablet, or capsule. The term "treating" refers to the administration of an effective amount of a composition of this invention to a subject, who has depression or anxiety, or a symptom or a predisposition of such a disease, with the purpose to cure, alleviate, relieve, remedy, or ameliorate depression, a major depressive disorder, an atypical depression, a bipolar disorder, a dysthymic disorder, anxiety, a panic disorder, a phobia, an obsessive-compulsive disorder, a posttraumatic stress disorder, or a generalized anxiety disorder, the symptoms of it, or the predispositions towards it. In a composition containing glabridin, resveratrol, and quercetin, recommended daily dosages are glabridin 20-3000 mg (preferably 40-2000 mg), resveratrol 50-3000 mg (preferably 100-2000 mg), and quercetin 50-4000 mg (preferably 100-3000 mg). In a composition containing isoquercetin, resveratrol, and quercetin, recommended daily dosages are isoquercetin 20-3000 mg (preferably 40-2000 mg), resveratrol 50-3000 mg (preferably 100-2000 mg), and quercetin 50-4000 mg (preferably 100-3000 mg). In a composition containing glabridin, resveratrol, and isoquercetin, recommended daily dosages are glabridin 20-3000 mg (preferably 40-2000 mg), resveratrol 50-3000 mg (preferably 100-2000 mg), and isoquercetin 50-4000 mg (preferably 100-3000 mg). A composition described above can further contain a daily dosage of vitamin C 20-2000 mg or a daily dosage of vitamin B3 1-200 mg.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for treating depression, the method comprising administering to a subject in need thereof an effective amount of a composition that includes three different compounds selected from the group consisting of glabridin, resveratrol, quercetin, and isoquercetin.

2. The method of claim 1, wherein the depression is a major depressive disorder, an atypical depression, a bipolar disorder, or a dysthymic disorder.

3. The method of claim 1, wherein the composition further includes vitamin C or vitamin B3.

4. The method of claim 1, wherein the composition includes glabridin, resveratrol, and isoquercetin, and the effective amount of the composition to be administered to the subject contains a daily dosage of 20-3000 mg glabridin, 50-3000 mg resveratrol, and 50-4000 mg isoquercetin.

5. The method of claim 4, wherein the daily dosage of glabridin is 40-2000 mg, the daily dosage of resveratrol is 100-2000 mg, and the daily dosage of isoquercetin is 100-3000 mg.

6. The method of claim 4, wherein the composition further includes vitamin C and vitamin B3 at a daily dosage of 20-2000 mg and 1-200 mg, respectively.

7. The method of claim 1, wherein the composition includes glabridin, resveratrol, and quercetin, and the effective amount of the composition to be administered to the subject contains a daily dosage of 20-3000 mg glabridin, 50-3000 mg resveratrol, and 50-4000 mg quercetin.

8. The method of claim 7, wherein the daily dosage of glabridin is 40-2000 mg, the daily dosage of resveratrol is 100-2000 mg, and the daily dosage of quercetin is 100-3000 mg.

9. The method of claim 7, wherein the composition further includes vitamin C and vitamin B3 at a daily dosage of 20-2000 mg and 1-200 mg, respectively.

10. The method of claim 1, wherein the composition includes isoquercetin, resveratrol, and quercetin, and the effective amount of the composition to be administered to the subject contains a daily dosage of 20-3000 mg isoquercetin, 50-3000 mg resveratrol, and 50-4000 mg quercetin.

11. The method of claim 10, wherein the daily dosage of isoquercetin is 40-2000 mg, the daily dosage of resveratrol is 100-2000 mg, and the daily dosage of quercetin is 100-3000 mg.

12. The method of claim 10, wherein the composition further includes vitamin C and vitamin B3 at a daily dosage of 20-2000 mg and 1-200 mg, respectively.

13. A method for treating anxiety, the method comprising administering to a subject in need thereof an effective amount of a composition that includes three different compounds selected from the group consisting of glabridin, resveratrol, quercetin, and isoquercetin.

14. The method of claim 13, wherein the anxiety is a panic disorder, a phobia, an obsessive-compulsive disorder, a posttraumatic stress disorder, or a generalized anxiety disorder.

15. The method of claim 13, wherein the composition further includes vitamin C or vitamin B3.

16. The method of claim 13, wherein the composition includes glabridin, resveratrol, and isoquercetin, and the effective amount of the composition to be administered to the subject contains a daily dosage of 20-3000 mg glabridin, 50-3000 mg resveratrol, and 50-4000 mg isoquercetin.

17. The method of claim 16, wherein the daily dosage of glabridin is 40-2000 mg, the daily dosage of resveratrol is 100-2000 mg, and the daily dosage of isoquercetin is 100-3000 mg.

18. The method of claim 13, wherein the composition further includes vitamin C and vitamin B3 at a daily dosage of 20-2000 mg and 1-200 mg, respectively.

19. The method of claim 13, wherein the composition includes glabridin, resveratrol, and quercetin, and the effective amount of the composition to be administered to the subject contains a daily dosage of 20-3000 mg glabridin, 50-3000 mg resveratrol, and 50-4000 mg quercetin.

20. The method of claim 19, wherein the daily dosage of glabridin is 40-2000 mg, the daily dosage of resveratrol is 100-2000 mg, and the daily dosage of quercetin is 100-3000 mg.

21. The method of claim 19, wherein the composition further includes vitamin C and vitamin B3 at a daily dosage of 20-2000 mg and 1-200 mg, respectively.

22. The method of claim 13, wherein the composition includes isoquercetin, resveratrol, and quercetin, and the effective amount of the composition to be administered to the subject contains a daily dosage of 20-3000 mg isoquercetin, 50-3000 mg resveratrol, and 50-4000 mg quercetin.

23. The method of claim 22, wherein the daily dosage of isoquercetin is 40-2000 mg, the daily dosage of resveratrol is 100-2000 mg, and the daily dosage of quercetin is 100-3000 mg.

24. The method of claim 22, wherein the composition further includes vitamin C and vitamin B3 at a daily dosage of 20-2000 mg and 1-200 mg, respectively.

* * * * *